United States Patent
Tesini

(10) Patent No.: US 7,335,022 B2
(45) Date of Patent: *Feb. 26, 2008

(54) DENTAL BITE IMPRESSION WAFER FOR IDENTIFICATION PURPOSES THAT ALSO CAPTURES DNA-BEARING MATERIALS

(76) Inventor: David A. Tesini, 13 Norcross St., Hopkinton, MA (US) 01748

( * ) Notice: Subject to any disclaimer, the term of this patent is extended or adjusted under 35 U.S.C. 154(b) by 157 days.

This patent is subject to a terminal disclaimer.

(21) Appl. No.: 11/031,447

(22) Filed: Jan. 7, 2005

(65) Prior Publication Data

US 2005/0123882 A1 Jun. 9, 2005

Related U.S. Application Data

(63) Continuation-in-part of application No. 10/098,982, filed on Mar. 15, 2002, now Pat. No. 7,252,507.

(60) Provisional application No. 60/535,063, filed on Jan. 8, 2004.

(51) Int. Cl.
*A61C 3/00* (2006.01)
(52) U.S. Cl. .................... 433/71; 433/214

(58) Field of Classification Search ................ 433/37, 433/48, 71, 214; 128/861, 862
See application file for complete search history.

(56) References Cited

U.S. PATENT DOCUMENTS

| | | | | |
|---|---|---|---|---|
| 2,183,624 | A * | 12/1939 | Schwartz | 433/71 |
| 4,324,547 | A * | 4/1982 | Arcan et al. | 433/71 |
| 4,472,140 | A * | 9/1984 | Lustig | 433/38 |
| 4,508,156 | A * | 4/1985 | Banks et al. | 164/35 |
| 4,541,803 | A * | 9/1985 | Adler | 433/141 |
| 4,624,640 | A * | 11/1986 | Tesini | 433/71 |
| 4,869,669 | A * | 9/1989 | Grubbs | 433/140 |
| 4,927,432 | A * | 5/1990 | Budinger et al. | 51/298 |
| 5,266,031 | A * | 11/1993 | Marigza | 433/71 |
| 5,503,552 | A * | 4/1996 | Diesso | 433/37 |
| 6,227,861 | B1 * | 5/2001 | Cartledge et al. | 433/215 |
| 6,913,517 | B2 * | 7/2005 | Prasad | 451/41 |

* cited by examiner

*Primary Examiner*—Ralph A. Lewis
(74) *Attorney, Agent, or Firm*—Brian M. Dingman; Mirick, O'Connell, DeMallie & Lougee, LLP

(57) ABSTRACT

A dental bite impression wafer that also captures the user's saliva and cheek cells. The wafer is made from a thermoplastic material that softens when warmed and that defines opposed posterior edges. The wafer carries one or more structures such as posts that are adapted to capture and retain the user's saliva and cheek cells.

8 Claims, 1 Drawing Sheet

DENTAL BITE IMPRESSION WAFER FOR IDENTIFICATION PURPOSES THAT ALSO CAPTURES DNA-BEARING MATERIALS

CROSS REFERENCE TO RELATED APPLICATION

This application claims priority of Provisional application Ser. No. 60/535,063, filed on Jan. 8, 2004. This application is also a continuation in part of application Ser. No. 10/098,982, filed on Mar. 15, 2002 now U.S. Pat. No. 7,252,507.

FIELD OF THE INVENTION

This invention relates to a dental bite impression wafer used for identification purposes.

BACKGROUND OF THE INVENTION

In providing means for identification of missing persons, photographs, fingerprints and dental chartings are commonly used. However, in the identification of a human body in which substantial decomposition has occurred, the use of fingerprints is often not possible, and in such cases dental chartings, if available, are often used.

Forensic odontology, the branch of dentistry which is concerned with identification of corpses by dental and oral characteristics, often plays a major role in the identification of missing persons and victims of crime and accidents.

However, if the victim has no dental record, identification by such means is obviously impossible. This is often the case with young children that are missing. A very large percentage of children of pre-school age have never visited a dentist, and a large percentage of those who have visited a dentist merely have an examination for tooth decay or other dental purposes. This record is seldom specific enough to serve as identifying means. Unless some restorative, preventive, or orthodontic treatment has been done that would provide a basis for identification, their dental chartings will have no distinguishable characteristics that might not be shared by many other individuals. No two individuals have the same dental bite characteristics.

In view of the fluoridation of public water supplies, which has reduced the amount of tooth decay in children, it is likely that in the future, even a lower percentage of children will have dental chartings that could be used for identification.

This is a serious problem, since according to the National Center for Missing and Exploited Children close to one million children are reported each year. Over 100,000 attempted abductions by non-family members are reported each year. Of these, 3,000 are successful, some children are returned alive, many are not, and some are never found.

Although bite impressions of wax or other material are often made of a persons teeth, such impressions are used for indicating the location of the upper and lower teeth in relation to each other. Also, they do not efficiently capture saliva for DNA and scent tracking. Wax bite impression wafers are disclosed in U.S. Pat. No. 4,624,640.

SUMMARY OF THE INVENTION

The invention features a wafer of thermoplastic material that, when heated to around 170° F., softens sufficiently so that a normal person can bite into the wafer for a specified period of time (typically until the wafer hardens sufficiently to maintain the impression; usually about 15-60 seconds) and create an impression of the teeth. The wafer also includes one or more artifacts that are adapted to capture saliva, which typically also includes exfoliated cheek cells that are in the saliva. The saliva and cheek cells are a source of the user's DNA. The wafer can be stored in an appropriate hard or soft container to retain a means of physical (teeth), chemical (scent of saliva) and biological (DNA) identification of the user, should such be necessary in the future. One example of a readily-available container would be a plastic bag. The container may contain a preservative-type substance that prolongs the usefulness of the saliva and/or cells.

In one embodiment, the invention comprises a dental bite impression wafer that also captures the user's saliva, comprising a thermoplastic wafer that softens when warmed and that defines opposed posterior edges, the wafer carrying one or more structures that are adapted to capture and retain at least the user's saliva. The structures may comprise a series of posts. The structures may comprise at least one opening. The structures may comprise at least one structure that accomplishes attraction of saliva and/or cells by capillary action.

In a particular embodiment, the dental bite impression wafer is generally U-shaped in plan with the posterior portion being formed by a pair of spaced legs, with the anterior portion connecting the spaced legs. The legs may have rounded ends. The wafer may further comprise a handle extending from the anterior portion.

The structures that are adapted to capture and retain saliva may be located along one or both sides of the wafer, and are preferably located along one or both posterior edges of the wafer. The wafer may further comprise one or more markings on the surface of the anterior portion of the wafer to assist in aligning the wafer with the teeth.

In another embodiment the invention features a dental bite impression wafer that also captures the user's saliva, comprising a molded thermoplastic wafer that softens when warmed and that defines opposed posterior edges, with at least one such edge defining one or molded, unitary features that are adapted to capture and retain at least the user's saliva. The molded, unitary features may comprise a series of posts.

In a further embodiment the invention features a dental bite impression wafer that also captures the user's saliva, comprising a molded thermoplastic wafer that softens when warmed, the wafer being generally U-shaped in plan with the posterior portion being formed by a pair of spaced legs having rounded ends and that define opposed posterior edges, with the anterior portion connecting the spaced legs, and a handle extending from the anterior portion, wherein at least one such edge defines one or molded, unitary features that are adapted to capture and retain at least the user's saliva.

BRIEF DESCRIPTION OF THE DRAWINGS

Other objects, features and advantages will occur to those skilled in the art from the following description of preferred embodiments and the accompanying drawings, in which.

DETAILED DESCRIPTION OF THE PREFERRED EMBODIMENTS OF THE INVENTION

Figure 1:
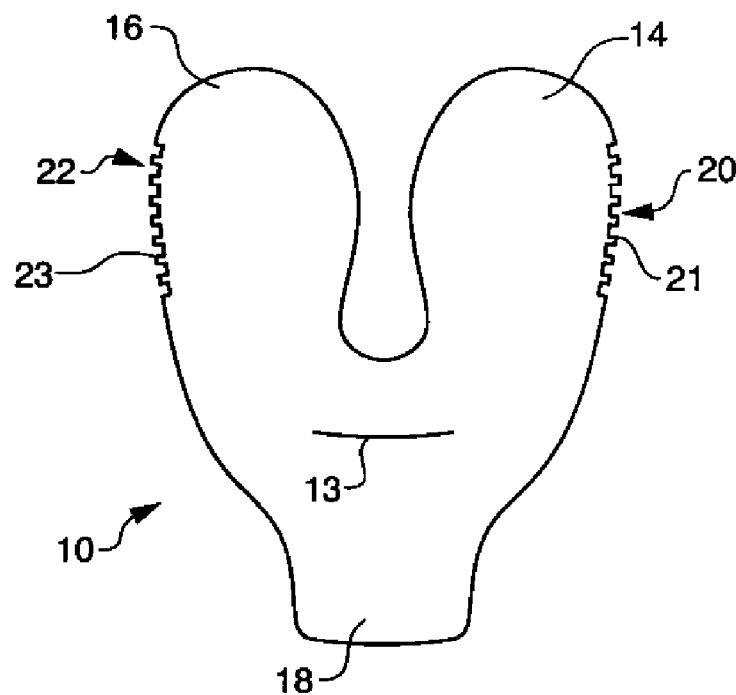
FIG. 1 is a top plan view, about actual size, of the most preferred embodiment of the wafer of this invention.

FIG. 1 is a top plan view, about actual size, of inventive wafer 10 of this invention. The wafer would be smaller for use with smaller children. Wafer 10 has posterior lobes 14 and 16 and anterior handle portion 18. Molded-in marking feature(s) 13 may be used to assist the person taking the impression in properly locating the wafer relative to the teeth (for example as a landing mark for the maxillary front incisors). Details of the general size, shape, materials, construction and usage of such a wafer, but without the specific features disclosed herein, may be found in U.S. Pat. No. 4,624,640, and U.S. patent application Ser. No. 10/098,982, filed on Mar. 15, 2002, both incorporated herein by reference.

A series of structures such as openings (in this case eight) in, or through the thickness of, wafer 10, in areas labeled 20 and 22 along the outer edges of lobes 14 and 16, respectively, create a series of pockets, openings or protruding posts 21 and 23, respectively, the ends of which preferably remain within the contour of wafer 10, although they may protrude beyond the contour or even be slightly withdrawn from what would be the contour if such features weren't present. These structures capture saliva and can also capture loose cells located in the mouth. Posts 21 and 23 also typically rub against the inside of the user's cheek, which can further loosen cells from the mucous membrane, which are then captured in the relevant features. Wafer 10 is preferably about 3 mm thick, and in the embodiment shown in the drawing the openings and posts are each about 1.4 mm wide.

If the wafer is kept in a plastic bag or another container, the saliva can be a source of scent for trained dogs. The saliva and cells can also be used as a source of DNA for identification purposes. Of course, the bite impression can also be used for identification purposes.

Alternatives to such openings and posts include roughened areas (preferably along the perimeter where the posts are shown in the drawing), a series of small spaced protrusions from the outer contour of the wafer, and one or more pockets anywhere on the portion of the wafer that enters the mouth, to capture saliva and cells. Another alternative construction includes one or more small tubes or similar structures that capture saliva/cells by capillary action, and can store such for longer periods of time than is the case when the captured biological materials are more exposed to the air.

Figure 2:
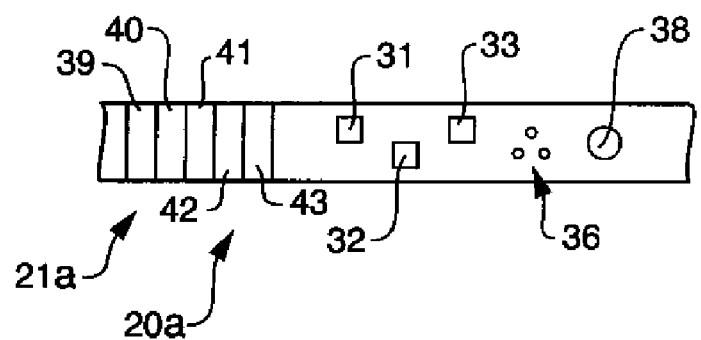
FIG. 2 is a side view of a portion of an outer lobe on a wafer of the invention, schematically depicting several different saliva/cell capturing features useful in the invention.

Several alternatives of features that capture saliva and/or cells, for inclusion in the inventive wafer, are shown in FIG. 2. Wafer area 20a depicts series 21a of alternating posts 39, 41 and 43 separated by openings 40 and 41, respectively. One of many possible alternative protruding post designs is shown by smaller, differently spaced posts 31-33. Another alternative is one or more small protruding (or inset) capillary tubes 36. Yet another alternative is different shaped (e.g. round) post or opening (cavity) 38. In a typical product application, only one style of such features is used in the wafer, although two or more may be used if desired. There are other possible shapes, styles and arrangements of such feature(s) that would be useful in the invention.

Wafer 10 is preferably injection molded of "Polyform" material available from Sammons Preston Rolyan, subsidiary of Patterson Dental in Cedarburg, Wis. This material has virtually no dimensional change over the entire operating temperature range (room temperature to around 170 F.). As a result, the impressed wafer will accurately record the size, shape and position of the teeth, which is information that can be used to reliably accomplish dental-based identification, should such be necessary. This material needs to be heated to a point at which it can be impressed by the bite (typically at least about 150 F.), and kept in the mouth for a time that is sufficient to allow the wafer to cool enough that it maintains the bite impression. The wafer can also be made fully or partially from other suitably-impressionable materials, such as wax or other thermoplastics.

The wafer need not have separate lobes, nor does it need two areas or structures that capture saliva and/or cells, as only one such area/structure, located anywhere on the wafer, would be sufficient to at least capture saliva. The saliva/cell-capture feature or features can alternatively be located on the inside of the lobes, or indeed in any location that enters the user's mouth.

Although specific features of the invention are shown in some drawings and not others, this is for convenience, as the various features may be combined in other manners in accordance with the claimed invention.

Other embodiments will occur to those skilled in the art and are within the following claims.

What is claimed is:

1. A method of using a dental bite impression wafer to capture a user's saliva, comprising:
   heating a thermoplastic wafer to soften the wafer, the wafer being generally U-shaped in plan with the posterior portion being formed by a pair of spaced legs and that defines opposed posterior edges and carrying one or more structures set into the wafer that accomplish attraction of saliva and/or cells by capillary action;
   biting to deform the wafer and create a dental bite impression in the wafer; and
   capturing, by capillary action, the user's saliva in the one or more structures set into the wafer.

2. The method of claim 1, further comprising capturing, loose cells located in the user's mouth in the one or more structures set into the wafer.

3. The method of claim 1, further comprising storing the thermoplastic wafer with the captured saliva in a container.

4. The method of claim 1, further comprising using the captured saliva for identification purposes.

5. The method of claim 1, where the one or more structures comprise one or more openings.

6. The method of claim 1, where the one or more structures comprise one or more pockets.

7. The method of claim 1, where the one or more structures comprise one or more protruding posts.

8. The method of claim 1, where the one or more structures comprise one or more roughened areas.

* * * * *